(12) United States Patent
Van Egmond

(10) Patent No.: US 7,402,720 B2
(45) Date of Patent: *Jul. 22, 2008

(54) DISTILLATION PROCESS FOR REMOVAL OF METHYL ACETYLENE AND/OR PROPADIENE FROM AN OLEFIN STREAM

(75) Inventor: Cor F. Van Egmond, Pasadena, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 642 days.

This patent is subject to a terminal disclaimer.

(21) Appl. No.: 10/325,396

(22) Filed: Dec. 19, 2002

(65) Prior Publication Data

US 2004/0122268 A1   Jun. 24, 2004

(51) Int. Cl.
*C07C 7/04*   (2006.01)
(52) U.S. Cl. .................. 585/802; 585/809; 585/836; 585/867; 203/3; 203/43; 203/68; 203/70
(58) Field of Classification Search ................ 585/802, 585/809, 836, 867; 203/3, 43, 68, 70
See application file for complete search history.

(56) References Cited

U.S. PATENT DOCUMENTS

| | | | |
|---|---|---|---|
| 2,657,243 A | 10/1953 | Giraitis et al. | 260/641 |
| 4,018,843 A | 4/1977 | Michaux et al. | 260/677 A |
| 4,087,477 A | 5/1978 | Tazuma et al. | 260/681.5 R |
| 6,066,238 A | 5/2000 | Perry | 203/3 |
| 6,124,517 A | 9/2000 | Kaminsky et al. | 585/829 |
| 6,559,248 B2 | 5/2003 | Hendriksen et al. | |
| 6,717,025 B1 | 4/2004 | Risch et al. | |
| 6,864,401 B2 * | 3/2005 | Van Egmond | 585/639 |
| 7,030,284 B2 | 4/2006 | Shutt | |
| 7,060,866 B2 | 6/2006 | Van Egmond et al. | |
| 2003/0199721 A1 | 10/2003 | Ding et al. | |
| 2004/0097760 A1 | 5/2004 | Risch et al. | |
| 2004/0122272 A1 | 6/2004 | Van Egmond et al. | |
| 2004/0122274 A1 | 6/2004 | Van Egmond et al. | |

* cited by examiner

*Primary Examiner*—Tam M. Nguyen

(57) ABSTRACT

The present invention provides a process for removing methyl acetylene and/or propadiene from a propylene stream and/or a butylene stream by two step fractionation. Methyl acetylene and/or propadiene avoids the use of a hydrogenation reactor and makes the methyl acetylene and/or propadiene recoverable from the process.

40 Claims, 2 Drawing Sheets

DISTILLATION PROCESS FOR REMOVAL OF METHYL ACETYLENE AND/OR PROPADIENE FROM AN OLEFIN STREAM

FIELD OF THE INVENTION

The present invention relates to a distillation process for removal of methyl acetylene and/or propadiene from an olefin-containing stream.

BACKGROUND OF THE INVENTION

Olefins are traditionally produced from petroleum feedstock by catalytic or steam cracking processes. These cracking processes, especially steam cracking, produce prime olefins such as ethylene and/or propylene from a variety of hydrocarbon feedstock. Ethylene and propylene are important commodity petrochemicals useful in many processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into prime olefins. This process is referred to as the oxygenate-to-olefin process. The preferred oxygenate for prime olefin production is methanol. The process of converting methanol to olefins is called the methanol-to-olefins process.

There are numerous technologies available for producing oxygenates, and particularly methanol, including fermentation or reaction of synthesis gas derived from natural gas, petroleum liquids, carbonaceous materials including coal, recycled plastics, municipal waste or any other organic material. The most common process for producing methanol is a two-step process of converting natural gas to synthesis gas. Then, synthesis gas is converted to methanol.

Generally, the production of synthesis gas involves a combustion reaction of natural gas, mostly methane, and an oxygen source into hydrogen, carbon monoxide and/or carbon dioxide. Synthesis gas production processes are well known, and include conventional steam reforming, autothermal reforming or a combination thereof.

Synthesis gas is then processed into methanol. Specifically, the components of synthesis gas (i.e., hydrogen, carbon monoxide and/or carbon dioxide) are catalytically reacted in a methanol reactor in the presence of a heterogeneous catalyst. For example, in one process, methanol is produced using a copper/zinc oxide catalyst in a water-cooled tubular methanol reactor.

The methanol is then converted to olefins in a methanol-to-olefins process and produces a reactor effluent stream. The reactor effluent stream contains desirable olefin product as well as byproducts. The byproducts are typically removed from any olefin product stream to make acceptable purity grades of olefin stream. Two very similar byproducts are methyl acetylene and propadiene. Methyl acetylene and/or propadiene (optionally referred to collectively as "MAPD") present a particular challenge for removal because they have similar relative volatility to propylene.

MAPD is destroyed by a hydrogenation reaction. Hydrogenation converts MAPD to propylene or propane. Hydrogenation reactors are not useful when it is desirable to recover the MAPD. Additionally, hydrogenation reactions are exothermic and carry a certain level of safety risk. Removing MAPD without the use of an exothermic reactor would be advantageous in certain instances.

U.S. Pat. No. 6,066,238 teaches a method of separating MAPD from an olefin stream. The first step provides an olefin stream comprising propylene and MAPD that optionally contains less than 1 wt. % $C_4$ hydrocarbon stream. Propane is added to the olefin stream. Then, the propane containing olefin stream is fractionated to produce an overhead stream comprising propylene and a bottoms fraction comprising propane and no more than 25 wt. % MAPD. The MAPD is then extracted from the propane with dimethyl formamide.

It would be desirable to separate MAPD from a propylene stream in a safe and effective way that avoids chemically converting the MAPD. The present invention satisfies these and other needs.

SUMMARY OF THE INVENTION

The present invention is a process for producing a propylene product stream and/or a butylene product stream from an olefin stream by removing MAPD from the propylene and/or butylene in a two-step fractionation process. The process eliminates the need for a MAPD hydrogenation converter. Furthermore, MAPD is always maintained at safe concentration levels by using propane and/or dimethyl ether as a diluent.

The process of one embodiment of the invention comprises providing an olefin stream comprising propylene, MAPD, and butylene. The olefin stream is fractionated in a first fractionation step. The first fractionation step produces a first overhead stream and a first bottoms stream. The first overhead stream comprises propylene and is substantially free of MAPD. The first bottoms stream comprises MAPD and butylene. The first bottoms stream is fractionated in a second fractionation step. The second fractionation step produces a second overhead stream and a second bottoms stream. The second overhead stream comprises MAPD. The second bottoms stream comprises butylene and is substantially free of MAPD.

There is a process according to another embodiment of the present invention that isolates a stream of MAPD from an effluent stream of an oxygenate-to-olefin reactor. The process comprises contacting an oxygenate feed stream with a molecular sieve catalyst. This contacting step produces an effluent stream that contains propane, propylene, MAPD, butylene and higher boiling point compounds. As used herein, the term "higher boiling point compounds" as it is used in the phrase "butylene and higher boiling point compounds" refer to compounds with a boiling point higher than butylene. The effluent stream is fractionated into the first overhead stream and a first bottoms stream. The first overhead stream contains about 25 wt. % or more propylene and about 1 wt. % or less MAPD based upon the total weight of the first overhead stream. The first bottoms stream contains MAPD, propane, butylene and higher boiling point compounds. At no time is propane added to the effluent stream before the effluent stream is fractionated. The first bottoms stream is fractionated in a second step. The second step fractionation produces a second overhead stream and a second bottoms stream, the second overhead stream contains propane and MAPD. The concentration of MAPD in the second overhead stream is from about 500 ppbw to about 2 wt. % based upon the total weight of the second overhead stream. The second bottoms stream contains butylene and higher boiling point compounds. One embodiment of the present invention is a process for producing polypropylene from natural gas. The process comprises the steps of: (a) converting the natural gas to an oxygenate thereby producing an oxygenate feed stream; (b) contacting the oxygenate feed stream with a molecular sieve catalyst thereby producing a reactor effluent comprising propylene, MAPD, propane, and butylene and higher boiling point compounds; (c) fractionating the effluent stream in a fractionation tower thereby producing a first overhead stream and a first bottoms stream, the first overhead stream contains propylene, the first bottoms stream contains propane, butylene, higher boiling point compounds and MAPD, wherein the amount of MAPD in the effluent stream as it enters the fractionation tower is greater than 1 ppmw (d) separating the first bottoms stream into a second overhead stream and a second bottoms stream, the second bottoms stream comprises MAPD and propane and a second bottoms stream comprising butylene and higher boiling point compounds; (e) isolating polymer grade propylene; and (f) converting the polymer grade propylene to polypropylene.

In another embodiment of the present invention there is a process for separating MAPD from a propylene stream. The process starts by providing a first stream comprising propylene, MAPD, and dimethyl ether. The first stream is separated into a second stream and a third stream. The second stream contains propylene and the third stream contains MAPD and dimethyl ether. The concentration of MAPD in the second stream is less than 10 ppmw based upon the weight of the second stream, the concentration of propylene in the third stream is less than 1 ppmw based upon the weight of the third stream.

DETAILED DESCRIPTION OF THE INVENTION

Introduction and Overview

Figure 1:
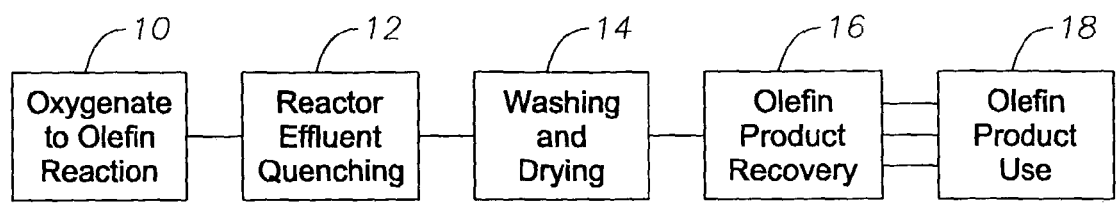
FIG. 1 illustrates the overall process of an oxygenate-to-olefins plant according to one embodiment of the present invention.

To aid in the understanding of the present invention, a brief overview of the stages of producing and using one or more olefin products from an oxygenate feed stream is discussed with reference to FIG. 1. The oxygenate-to-olefin reaction stage 10 converts an oxygenate feed stream into a gaseous output stream comprising one or more olefin(s). The gaseous output stream of an oxygenate-to-olefin reactor is defined as the effluent stream. The reactor effluent stream is particularly the gaseous output stream from the point this stream leaves the reactor to the point the stream enters a quench device.

Following the oxygenate-to-olefin reaction stage, the reactor effluent stream passes through an effluent quenching stage 12 The effluent quenching stage 12 cools the reactor effluent stream and removes water and catalyst fines from the reactor effluent stream. Included in the effluent quenching stage is optional compression of the quenched effluent stream.

Figure 3:
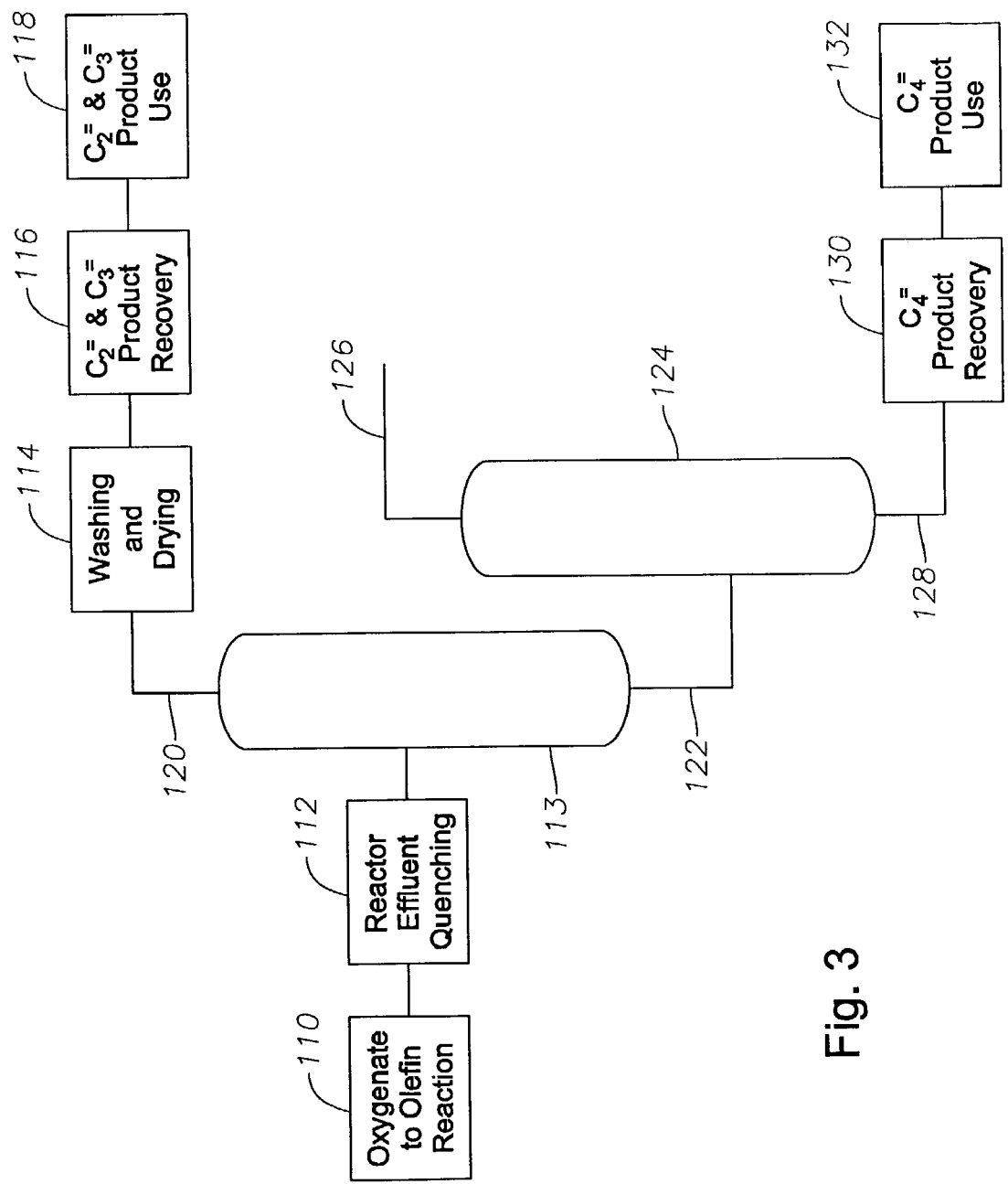
FIG. 3 illustrates a process scheme for separating MAPD from an olefin product stream in a $C_3$ splitter before the olefin product stream is washed to remove acid gas components and/or dried to remove water.

The quenched effluent stream then undergoes a washing and drying stage 14 to produce a dried effluent stream. Washing the quenched effluent stream removes acid components of the effluent stream, such as $CO_2$. Drying removes water that is saturated in the quenched effluent stream. Optionally, the washing and drying stage includes processing steps to remove additional oxygenates. According to an optional embodiment of the invention, there is a two-step fractionation process of one embodiment of the present invention illustrated in FIG. 3 and discussed below in greater detail.

The dried effluent stream then undergoes a olefin product recovery stage 16. Particularly, prime olefins, i.e. ethylene, propylene and butylene are recovered in olefin product streams in acceptable grades of purity for their particular applications or end uses. In the product recovery stage 16, MAPD is removed from a propylene-containing stream according to one embodiment of the invention illustrated in FIG. 2.

Finally the olefin product streams pass through an olefin product use stage 18. In the olefin product use stage 18, the olefin product streams are used in a polymerization process to make polyolefin products. For a more complete understanding of the integrated process of producing and using olefin product streams from an oxygenate feed stream is discussed below in greater detail.

The Oxygenate-to-Olefin Reaction

An oxygenate feed stream is fed into an oxygenate-to-olefin reactor producing a reactor effluent stream. The oxygenate-to-olefin reactor uses a catalyst and particularly a molecular sieve catalyst made of a molecular sieve catalyst composition. Molecular sieve catalysts are useful for converting a feed stream that contains one or more aliphatic-containing compounds. The one or more aliphatic-containing compounds include alcohols, amines, carbonyl compounds for example aldehydes, ketones and carboxylic acids, ethers, halides, mercaptans, sulfides, and the like, and mixtures thereof. The aliphatic part of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkylamines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feed stream is an oxygenate feed stream. Particularly, an oxygenate feed stream is a feed stream that comprises one or more organic compound(s) containing at least one oxygen atom. In the most preferred embodiment of the invention, the oxygenate in the oxygenate feed stream is one or more alcohol(s), preferably aliphatic alcohol(s) where the aliphatic part of the alcohol(s) has from 1 to 20 carbon atoms, preferably from 1 to 10 carbon atoms, and most preferably from 1 to 4 carbon atoms. The alcohols that are useful in the oxygenate feed stream include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, diisopropyl ether, formaldehyde, dimethyl carbonate, dimethyl ketone, acetic acid, and mixtures thereof.

In the most preferred embodiment, the oxygenate feed stream comprises oxygenates selected from one or more of methanol, ethanol, dimethyl ether, diethyl ether or a combination thereof, more preferably methanol and dimethyl ether, and most preferably methanol.

In one embodiment, the oxygenate feed stream is produced from an integrated process for producing oxygenates, particularly alcohols, from a hydrocarbon feedstock, preferably a hydrocarbon gas feedstock, more preferably methane and/or ethane. The first step in the process is passing the gaseous hydrocarbon feedstock, preferably in combination with a water stream, to a synthesis gas production zone to produce a synthesis gas stream containing synthesis gas. Synthesis gas production is well known, and typical synthesis gas temperatures are in the range of from about 700° C. to about 1200° C. and synthesis gas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas.

Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide, nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol. This purified oxygenate containing stream is used in one embodiment as the oxygenate feed stream. Non-limiting examples of a process for producing an oxygenate feed stream from hydrocarbons and using it to produce olefins is described in EP-B-0 933 345, which is herein fully incorporated by reference.

The feed stream, preferably an oxygenate feed stream, in one embodiment, contains one or more diluents, typically used to reduce the concentration of the active ingredients in the feed stream, and are generally non-reactive to the active ingredients in the feed stream or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feed stream entering into a reactor or added directly into the reactor, or added with a molecular sieve catalyst composition. In one embodiment, the amount of diluent in the feed stream is in the range of from about 1 to about 99 mole percent, preferably from about 1 to 80 mole percent, more preferably from about 5 to about 50, and most preferably from about 5 to about 25 diluent based on the total number of moles of the active components of the feed stream plus diluent in the feed stream.

In one embodiment, other hydrocarbons are added to the feed stream, preferably oxygenate feed stream, either directly or indirectly, and include olefin(s), paraffin(s), aromatic(s) (see for example U.S. Pat. No. 4,677,242, addition of aromatics) or mixtures thereof, preferably propylene, butene, pentene, and other hydrocarbons having 4 or more carbon atoms, or mixtures thereof.

The various feed streams, preferably oxygenate feed streams, discussed above are converted primarily into one or more olefin(s). The olefin(s) or olefin monomer(s) produced from the feed stream typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or non-conjugated dienes, polyenes, vinyl monomers and cyclic olefins.

In the most preferred embodiment, the feed stream, preferably an oxygenate feed stream, is converted in the presence of a molecular sieve catalyst composition into olefin(s) having 2 to 6 carbons atoms, preferably 2 to 4 carbon atoms. Most preferably, the olefin(s), alone or combination, are converted from an oxygenate feed stream preferably containing an alcohol, and most preferably methanol, to the preferred olefin(s) ethylene propylene and/or butylene often referred to as prime olefin(s).

The most preferred oxygenate-to-olefins process is the methanol-to-olefins process. In a methanol-to-olefin process, a methanol containing feed stream is converted to olefins in the presence of a methanol-to-olefins catalyst or catalyst composition. In one embodiment, the methanol-to-olefins catalyst or catalyst composition is molecular sieve catalyst composition.

In one embodiment of the process for conversion of an oxygenate feed stream, the amount of olefin(s) produced based on the total weight of hydrocarbon produced is greater than 50 weight percent, preferably greater than 60 weight percent, more preferably greater than 70 weight percent, and most preferably greater than 75 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

As noted, oxygenate-to-olefin processes use molecular sieve catalysts or molecular sieve catalyst compositions. The molecular sieve catalysts compositions have molecular sieve and binder and/or matrix material. The molecular sieve catalysts are prepared according to techniques that are known to a person of ordinary skill in the art.

Molecular sieve include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, AFO, AEL, EUO, HEU, FER, MEL, MFI, MTW, MTT, TON, EMT, FAU, ANA, BEA, CFI, CLO, DON, GIS, LTL, MER, MOR, MWW and SOD and substituted forms thereof; and the large pore molecular sieves. Preferably the molecular sieve is a zeolitic or zeolitic-type molecular sieve. Alternatively, the preferred molecular sieve is an aluminophosphate (ALPO) molecular sieves and/or silicoaluminophosphate (SAPO) molecular sieves and substituted, preferably metal substituted, ALPO and/or SAPO molecular sieves including the molecular sieves that are intergrowth materials having two or more distinct phases of crystalline structures within one molecular sieve composition.

Binder materials that are useful alone or in combination include various types of hydrated alumina, silicas, and/or other inorganic oxide sol. In one embodiment, the binders are alumina sols including include Nalco 8676 available from Nalco Chemical Co., Naperville, Ill., and Nyacol available from The PQ Corporation, Valley Forge, Pa.

Matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite.

The process for converting a feed stream, especially an oxygenate feed stream in the presence of a molecular sieve catalyst composition is carried out in a reactor process. In one embodiment, the reactor process is a fixed bed reactor process, a fluidized bed reactor process, preferably a continuous fluidized bed reactor process, and most preferably a continuous high velocity fluidized bed reactor process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred oxygenate-to-olefin reactor is a riser reactor. Riser reactors are generally described in *Riser Reactor, Fluidization and Fluid-Particle Systems,* pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor, a regenerator, and a recovery system.

The reactor or reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Feed stream, preferably an oxygenate feed stream, optionally with one or more diluent(s), is fed to the one or more riser reactor(s) in which a zeolite, zeolite-type molecular sieve catalyst, silicaluminophosphate catalyst composition or coked version thereof is introduced. In one embodiment, the molecular sieve catalyst composition or coked version thereof is contacted with a liquid or gas, or combination thereof, prior to being introduced to the riser reactor(s). Preferably, the liquid is water or methanol, and the gas is an inert gas such as nitrogen.

In an embodiment, the feed stream, preferably an oxygenate feed stream, is feed into the reactor in the vapor form or the liquid form. The vapor form of the feed stream is referred to as a vapor feed stream. The feed stream in the liquid form is referred to as the liquid feed stream. The amount of liquid feed stream fed separately or jointly with a vapor feed stream, to a reactor system is in the range of from 0.1 weight percent to about 85 weight percent, preferably from about 1 weight percent to about 75 weight percent, more preferably from about 1 weight percent to about 10 weight percent based on the total weight of the feed stream including any diluent contained therein. The liquid and vapor feed streams are preferably of similar composition, or contain varying proportions of the same or different feed stream compositions with varying proportions of the same or different diluent compositions.

The feed stream, preferably an oxygenate feed stream, entering the reactor system is preferably converted, partially or fully, in the first reactor zone into an effluent stream that enters the disengaging vessel along with a coked molecular sieve catalyst composition. In the preferred embodiment, particle size separators within the disengaging vessel are designed to separate catalyst particles from the effluent stream containing one or more olefin(s) within the disengaging zone as well as separate catalyst particles from catalyst fines entrained in the effluent stream. Cyclones are preferred particle size separators. Cyclones generally retain catalyst particles but do not retain catalyst fines.

Gravity effects within the disengaging vessel will also separate the catalyst particles from the effluent stream. Other methods for separating the catalyst particles from the effluent stream include the use of plates, caps, elbows, and the like.

In one embodiment, the effluent stream as it leaves the reactor 22 comprises ethylene and propylene, $C_4+$ olefins, methane, $C_2+$ parafins, water, unreacted oxygenate feed stream, and oxygenate hydrocarbons. In another embodiment, the reactor effluent stream comprises from about 30 wt. % to about 70 wt. % water, preferably, from about 35 wt. % to about 70 wt. % water; more preferably from about 40 wt. % to about 65 wt. % water expressed as a percentage of the total weight of the reactor effluent stream. According to another aspect of the invention, there are catalyst fines entrained in the reactor effluent stream. The weight of catalyst in the reactor effluent stream, including catalyst fines, expressed as a percent of the weight of the reactor effluent stream plus entrained catalyst comprises about 5 wt. % or less, preferably about 2 wt. % or less, more preferably about 1 wt % or less; even more preferably about 0.5 wt % or less. In another embodiment, the weight of the catalyst, including catalyst fines, expressed as a percentage of the weight of the reactor effluent stream plus entrained catalyst comprises from about 0.00005 wt % to about 0.5 wt %; preferably; from about 0.0001 wt % to about 0.1 wt %.

In another embodiment, about 10 wt. % or less, preferably about 5 wt. % or less, most preferably about 1 wt. % or less of the catalyst fines in the reactor effluent stream has a particle size greater than 40 microns, based upon the total weight of catalyst fines in the reactor effluent stream.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 hr$^{-1}$ to about 20,000 hr$^{-1}$ based on the volume of gas to volume of coked molecular sieve catalyst composition, preferably at an elevated temperature from about 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C., and most preferably from about 350° C. to about 550° C.

The conversion pressure employed in the conversion process, specifically within the reactor system, varies over a wide range including autogenous pressure. The conversion pressure is based on the partial pressure of oxygenate in the oxygenate feed stream exclusive of any diluent therein. Typically, the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting an oxygenate feed stream in the presence of a molecular sieve catalyst composition within a reaction zone, is defined as the total weight of the oxygenate feed stream excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr$^{-1}$ to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of an oxygenate feed stream containing methanol and dimethyl ether is in the range of from about 20 hr$^{-1}$ to about 300 hr$^{-1}$.

The superficial gas velocity (SGV) of an oxygenate feed stream including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate-to-olefin(s) using a silicoaluminophosphate molecular sieve catalyst composition, the process is operated at a WHSV of at least 20 hr$^{-1}$ and a Temperature Corrected Normalized Methane Selectivity (TCNMS) of less than 0.016, preferably less than or equal to 0.01. See, for example, U.S. Pat. No. 5,952,538 that is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The process of converting oxygenates to olefins with certain molecular sieve catalyst compositions causes carbonaceous deposits or "coke" to build up on the catalyst. In one embodiment, the cooked molecular sieve catalyst or coked catalyst is withdrawn from a disengaging vessel of the reactor, preferably by one or more cyclones(s). The coked catalyst is introduced into a regenerator. In the regenerator, the cooked catalyst is contacted with a regeneration medium, preferably a gas containing oxygen, under general regeneration conditions of temperature, pressure, and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The preferred residence time of a catalyst, including a molecular sieve catalyst, in the regenerator is in the range of from about one minute to several hours, most preferably about one minute to about 100 minutes. In one embodiment, the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with coked catalyst. Also, in another embodiment, fresh molecular sieve catalyst is added to the regenerator containing a regeneration medium of oxygen and water as described in U.S. Pat. No. 6,245,703, which is herein fully incorporated by reference.

According to one embodiment, the burning of catalyst including catalyst particles in the regenerator produces a flue gas and regenerated catalyst, including regenerated catalyst particles and regenerated catalyst fines. The flue gas is defined as the gaseous output of the regenerator. The flue gas is separated from the regenerated catalyst particles by a particle size separator such as a cyclonic separator or cyclone. The cyclones retain catalyst particles but allow the flue gas to exit the regenerator. Additionally, regenerated catalyst fines are carried in the flue gas and leave the regenerator.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst from the regeneration system and passing the regenerated catalyst through a catalyst cooler that forms a cooled regenerated catalyst. The catalyst cooler, in an embodiment, is a heat exchanger that is located either internal or external to the regeneration system.

In one embodiment, the cooler regenerated catalyst is returned to the regenerator in a continuous cycle, alternatively, (see U.S. patent application Ser. No. 09/587,766 filed Jun. 6, 2000) a portion of the cooled regenerated catalyst is returned to the regenerator vessel in a continuous cycle, and another portion of the cooled regenerated catalyst is returned to the riser reactor(s), directly or indirectly, or a portion of the regenerated catalyst or cooled regenerated catalyst is contacted with by-products within the effluent stream (PCT WO 00/49106 published Aug. 24, 2000), which are all herein fully incorporated by reference. In another embodiment, a regenerated catalyst contacted with an alcohol, preferably ethanol, 1-propanol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are in disclosed U.S. Pat. No. 6,290,916 (controlling moisture), which is herein fully incorporated by reference.

The regenerated catalyst particles are withdrawn from the regenerator and returned to the reactor. In one embodiment, the regenerated catalyst particles that are withdrawn from the regeneration system, preferably from the catalyst cooler, are combined with a fresh catalyst and/or re-circulated catalyst and/or feed stream and/or fresh gas or liquids, and returned to the riser reactor(s). In another embodiment, the regenerated catalyst withdrawn from the regeneration system is returned to the riser reactor(s) directly, optionally after passing through a catalyst cooler. In one embodiment, a carrier, such as an inert gas, vapor feed stream, steam or the like, semi-continuously or continuously, facilitates the introduction of the regenerated catalyst to the reactor or reactor system, preferably to the one or more riser reactor(s).

In one embodiment, the optimum level of coke on the catalyst composition in the reaction zone is maintained by controlling the flow of the regenerated catalyst or cooled regenerated catalyst from the regeneration system to the reactor system. There are many techniques for controlling the flow of a catalyst described in Michael Louge, *Experimental Techniques, Circulating Fluidized Beds,* Grace, Avidan and Knowlton, eds., Blackie, 1997 (336-337), which is herein incorporated by reference. This is referred to as the complete regeneration mode. In another embodiment, the optimum level of coke on the molecular sieve catalyst in the reaction zone is maintained by controlling the flow rate of the oxygen-containing gas flow to the regenerator. This is referred to as the partial regeneration mode.

Coke levels, or the level of carbonaceous deposits on the catalyst, are measured by withdrawing from the conversion process the catalyst composition at a point in the process and determining its carbon content.

In one preferred embodiment, the catalyst in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of catalyst. See for example U.S. Pat. No. 6,023,005, which is herein fully incorporated by reference. It is recognized that the catalyst in the reaction zone is made up of a mixture of regenerated catalyst and catalyst that has ranging levels of carbonaceous deposits. The measured level of carbonaceous deposits thus represents an average of the levels an individual catalyst particle.

As noted above, the reactor effluent stream leaves the reactor through particle size separators. The reactor effluent stream optionally passes through a heat exchanger system. According to one embodiment the heat exchanger system comprises one or more heat exchangers, preferably two to four heat exchangers, most preferably two or three heat exchangers. Optionally, the heat exchanger system cools the effluent stream to produce a cooled effluent stream. The cooled effluent stream is withdrawn from the heat exchanger system and is sent to a quench device.

Reactor Effluent Quenching

The oxygenate-to-olefin process forms a substantial amount of water as a byproduct. Furthermore, a substantial amount of catalysts are carried in the effluent stream. Water and catalyst fines can be removed from the reactor effluent stream by a quench device. A "quench device" is a device for removing a portion of the reactor effluent stream by establishing a sufficient quantity of a liquid phase in contact with the reactor effluent stream which condenses at least a portion of the material in the reactor effluent stream. One example of a quench device in an oxygenate-to-olefin product stream is found in U.S. Pat. No. 6,121,504 (direct product quench). The liquid matter that contacts the reactor effluent stream and causes the condensation is called a "quench medium."

In a quench device, at least a portion of the reactor effluent stream is rapidly condensed through contact with a quench medium in the liquid state (a form of what is typically called "direct contact heat transfer"). When quenching in a quench device, at least a portion of the reactor effluent stream remains in a gaseous state. A portion of the reactor effluent stream condenses to form a liquid fraction which is withdrawn from the quench device as a first liquid stream in one embodiment. The portion of the reactor effluent stream in a gaseous state is separated from the liquid fraction.

The portion of the reactor effluent stream that is gaseous under quenching conditions typically comprises prime olefins, dimethyl ether, methane, CO, $CO_2$, ethane, propane, and any water and unreacted oxygenate feed stream that is not condensed during the operation of the quench device. These gaseous compounds in the reactor effluent stream generally pass through the quench device and form the quenched effluent stream. The quenched effluent stream is defined as the effluent stream after at least one stage of quenching. The compounds in the reactor effluent stream that are liquid under quenching conditions typically comprises water, a portion of the unreacted oxygenate feed stream (typically methanol), and a small portion of the oxygenate conversion byproducts, e.g. heavy hydrocarbons ($C_5+$). These compounds form a quench bottoms stream or a liquid fraction. Additionally, quench medium contacts the catalyst fines in the reactor effluent stream and washes the catalyst fines into the liquid fraction. Thus, the liquid fraction contains catalyst fines.

According to one embodiment of the present invention, a quench tower is employed as a quench device. According to one embodiment the quench device has one or more stages, preferably one to four stages, most preferably one to three stages. A one stage quench is disclosed in U.S. Pat. No. 6,121,504, the content of which is incorporated fully by reference. A two stage quench is disclosed in U.S. Pat. No. 6,403,854, the content of which is incorporated fully by reference.

In a particular embodiment, the quench medium is water. In another embodiment, the quench medium is a portion of the water that has been recovered from the quench device and cooled (thus reintroduced to the quench tower), and which contains at least a portion of the catalyst fines separated from the gaseous effluent stream and is referred to as recovered quench medium. According to one embodiment, the quench is operated under conditions such that the cooled process gas then enters the quench device where effluent water is condensed, acetic acid is neutralized and some heavy oxygenates ($C_3$-$C_4$+ aldehydes, ketones & alchols) are rejected.

As previously described the reactor effluent stream is quenched to remove catalyst fines and water that are present in the reactor effluent stream and produces a quenched effluent stream.

In an embodiment of the invention, the quenched effluent stream contains both ethylene and propylene. Desirably, the quenched effluent stream contains about 50 wt. % or more, preferably from about 50 wt. % to about 95 wt. %, more preferably from about 55 wt. % to about 90 wt. %, and most preferably from about 60 wt. % to about 85 wt. % ethylene and propylene based upon the total weight of the quenched effluent stream as it leaves the quench device.

In another embodiment, the quenched effluent stream comprises about 25 wt. % or more from about 25 wt. % ethylene to about 75 wt. %, more preferably from about 30 wt. % to about 60 wt. %, and most preferably from about 35 wt. % to about 50 wt. % ethylene based upon the total weight of the quenched effluent stream after it leaves the quench device.

In another embodiment, the quenched effluent stream comprises about 20 wt. % or more, preferably from about 20 wt. % to about 70 wt. %, more preferably from about 25 wt. % to about 50 wt. %, and most preferably from about 30 wt. % to about 40 wt. % propylene based upon the total weight of the quenched effluent stream after it leaves the quench device.

It is desirable that the quenched effluent stream contains a relatively low concentration of ethane, preferably a lower concentration of ethane than propane. Preferably, the olefin stream comprises about 4 wt. % or less, more preferably about 3 wt. % or less, and most preferably about 2 wt. % or:less ethane based upon the total weight of the quenched effluent stream after it leaves the quench device.

It is also desirable that the quenched effluent stream contains a relatively low concentration of propane. Preferably, the olefin stream comprises about 5 wt. % or less, more preferably about 4 wt. % or less, and most preferably about 3 wt. % or less propane based upon the total weight to the quenched effluent stream after it leaves the quench device.

In one embodiment, the quenched effluent stream that is provided comprises about 50 wt. % or less, preferably about 20 wt. % or less, more preferably about 10 wt. % or less, and most preferably about 5 wt. % or less dimethyl ether. In an embodiment, the provided olefins stream will contain at about 100 wppm or more, preferably about 500 wppm dimethyl ether or more, and more preferably about 1,000 wppm or more dimethyl ether based upon the total weight of the quenched effluent stream as it leaves the quench device.

In another embodiment of the invention, the quenched effluent stream is further processed by compression, preferably multi-staged compression. Two, three, four or more stages can be used, with two or three stages being preferred.

Desirably, the quenched effluent stream is compressed to a pressure that is greater than that at which the oxygenate-to-olefin reaction process is carried out. Preferably, the olefin stream is compressed to a pressure of about 30 psia (207 kPa) or more, more preferably about 50 psia (345 kPa) or more, most preferably about-100 psia (689 kPa) or more. High-pressure ranges are particularly preferred, with the upper limit being a practical one based on cost of design and ease of operation. In an embodiment, the pressure is from about 1,000 psia (6,895 kPa) to about 5,000 psia (34,450 kPa), preferably from about 750 psia (5171 kPa) to about 5,000 psia (34,450 kPa), more preferably from about 500 psia (3447 kPa) to about 5,000 psia (34,450 kPa).

Following compression, the quenched effluent stream is further processed by washing to remove acid gases and alternatively other oxygenates and drying to remove water as described below.

Washing and Drying

An acid gas wash optionally is used to remove acid gas from the quenched effluent stream in the first fraction by contacting the first fraction with an acid gas absorbent or adsorbent. Non-limiting examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred.

Aqueous amine solutions, which are useful in one embodiment this invention, contain any amine compound or compounds suitable for acid gas absorption. Non-limiting examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations range from about 0.5 to about 8 moles of amine per liter of aqueous solution in one embodiment.

Piperazine and/or monomethylethanolamine (MMEA) in one embodiment are added to aqueous amine solutions to enhance their absorption capabilities. These additives are included in the aqueous solution at a concentration of from about 0.04 to about 2 moles per liter of aqueous solution.

Caustic compounds, which are used in one embodiment of this invention, are alkaline compounds, which are effective in removing acid gas from an olefin stream. Non-limiting examples of such alkaline compounds include sodium hydroxide and potassium hydroxide.

Following acid gas treating, it is desirable to remove additionally entrained material in the quenched effluent stream using a water wash. Conventional equipment is optionally used. It is desirable, however, to further remove additional water from the quenched effluent streams.

This invention further includes an optional drying embodiment. In this embodiment, a solid or liquid drying system is used to remove water and/or additional oxygenated hydrocarbon from the quenched effluent stream.

In the solid drying system, the quenched effluent stream having been optionally acid gas treated and water washed, is contacted with a solid adsorbent to further remove water and oxygenated hydrocarbon to very low levels. Typically, the adsorption process is carried out in one or more fixed beds containing a suitable solid adsorbent.

Adsorption is useful for removing water and oxygenated hydrocarbons to very low concentrations, and for removing oxygenated hydrocarbons that are not normally be removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of contaminants being removed. Non-limiting examples of solid adsorbents for removing water and various polar organic compounds, such as oxygenated hydrocarbons and absorbent liquids, include aluminas, silica, 3 A molecular sieves, 4 A molecular sieves, and alumino-silicates. Beds containing mixtures of these sieves or multiple beds having different adsorbent solids optionally is used to remove water, as well as a variety of oxygenated hydrocarbons.

In one embodiment of this invention, one or more adsorption beds is arranged in series or parallel. In one example of a series arrangement, a first bed is used to remove the smallest and most polar molecules, which are the easiest to remove. Subsequent beds for removing larger less polar oxygenated species are next in series. As a specific example of one type of arrangement, water is first selectively removed using a 3 A molecular sieve. This bed is then followed by one or more beds containing one or more less selective adsorbents such as a larger pore molecular sieve e.g. 13 X and/or a high surface area active alumina such as Selexorb CD (Alcoa tradename).

In another embodiment, the first bed is a 3.6 A molecular sieve capable of selectively removing both water and methanol. This bed is then followed by one or more 13 X or active alumina beds as described above.

The adsorbent beds typically are operated at ambient temperature or at elevated temperature as required, and with either upward or downward flow. Regeneration of the adsorbent materials are often carried out by conventional methods including treatment with a stream of a dry inert gas such as nitrogen at elevated temperature.

In the liquid drying system, a water absorbent is used to remove water from the quenched effluent stream. The water absorbent of one embodiment is any liquid effective in removing water from an olefin stream. Preferably, the water absorbent is a polyol or an alcohol, such as ethanol or methanol.

Preferably the olefin from the adsorption beds contains less than about 100 wppm water, more preferably less than about 10 wppm, and most preferably less than 1 wppm. Preferably less than about 10 wppm dimethyl ether is present in the stream leaving the adsorption beds, more preferably less than about 5 wppm, and most preferably less than about 1 wppm. The step of acid washing and drying produces an olefin stream.

Olefin Product Recovery

The olefin stream from the dryer, is further processed to isolate and purify components in the effluent stream, particularly, prime olefins (i.e. ethylene, propylene, and butylene. There are many well-known recovery systems, techniques and sequences that are useful in separating and purifying an olefin stream into one or more olefin product streams, preferably, high purity olefin product streams.

As noted the object of one embodiment of the present invention is to isolate prime olefin product streams that contains a $C_X$ olefin, wherein x is an integer from 2 to 4, in an amount that is about 80 wt. % or more, preferably about 90 wt. % or more, more preferably about 95 wt. % or more based upon the total weight of the high purity prime olefin stream. It is most preferable to isolate high purity prime olefin streams that contain $C_X$ olefin, wherein x is an integer from 2 to 4, in an amount greater than about 99 wt. % or more, based on the total weight of the high purity olefin stream. The olefin product stream has a purity grade that is selected for the particular application or end use of the olefin product stream. To accomplish the isolation of prime olefin streams, and preferably high purity prime olefin streams, a fractionation train is provided. The fractionation train comprises a demethanizer, a $C_2$ splitter, a deethanizer, a $C_3$ splitter, a depropanizer, a debutanizer, and a debutyleneizer. A demethanizer is a fractionation tower that separates methane and compounds with a boiling point lower than methane from ethylene and compounds with boiling point higher than ethylene. A $C_2$ splitter is a fractionation tower that separates ethylene and compounds with a boiling point lower than ethylene from ethane and compounds with boiling point higher than ethane. A deethanizer is a fractionation tower that separates ethane and compounds with a boiling point lower than ethane from propylene, and compounds with boiling point higher than propylene. A $C_3$ splitter is a fractionation tower that separates propylene and compounds with a boiling point lower than propylene from propane and compounds with boiling point higher than propane.

A depropanizer is a fractionation tower that separates propane and compounds with a boiling point lower than propane from butylene and compounds with boiling point higher than butylene. A debutylencizer is a fractionation tower that separates butylene and compounds with a boiling point lower than butane from butane and compounds with boiling point higher than butane.

Figure 2:
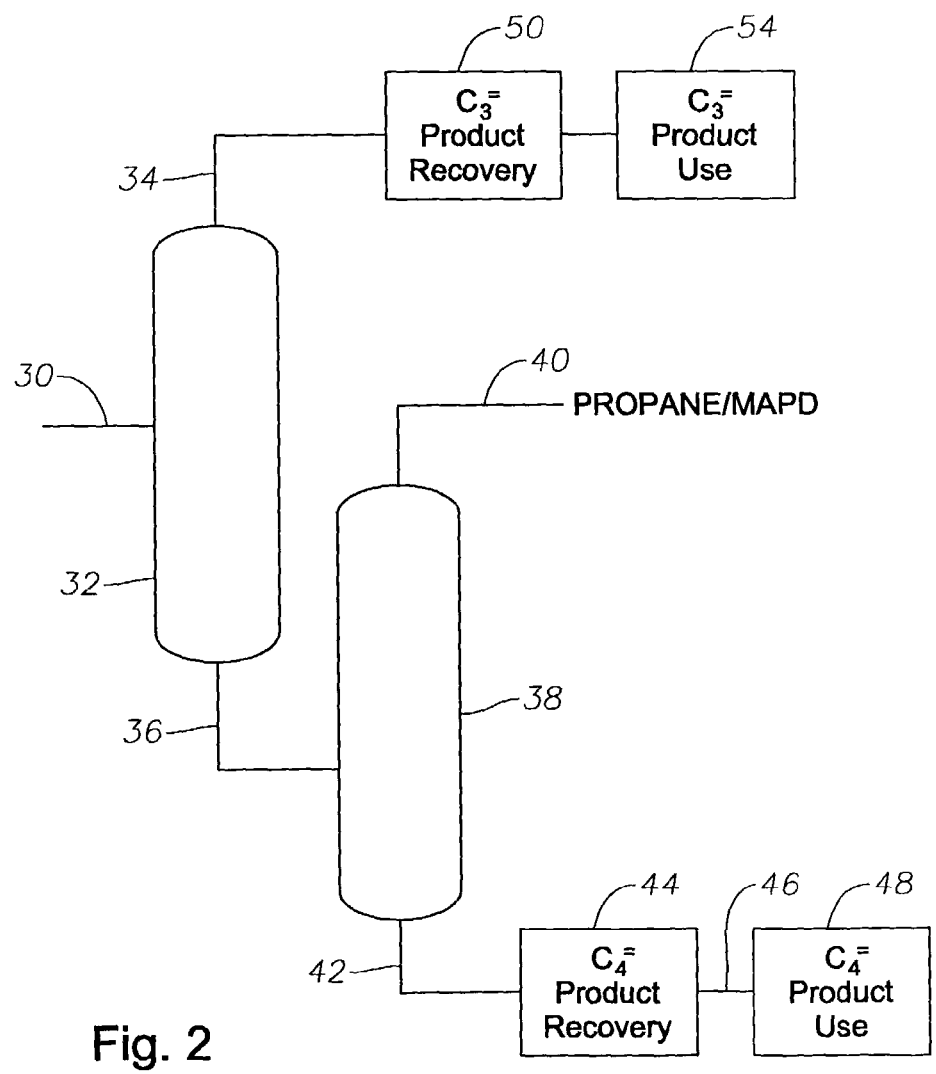
FIG. 2 illustrates a process scheme for separating MAPD from a propylene stream during olefin recovery according to one embodiment of the present invention.

According to one embodiment described in FIG. 2, an olefin stream is provided comprising propane, propylene, MAPD, and butylene. Optionally, the olefin stream contains dimethyl ether. Additionally and optionally, the olefin stream contains ethylene, ethane, and methane. Alternatively, the two-step fractionation process of one embodiment of the present invention is downstream from a demethanizer.

According to one embodiment, the weight ratio of MAPD to butylene in the olefin stream ranges from about 1:100 to about 1:100,000; typically from about 1:10,000 to about 50,000; optionally from about 1:15,000 to about 1:20,000. According to one embodiment, the weight ratio of MAPD to propylene in the olefin stream ranges from about 1:20,000 to about 1:200,000; typically from about 1:50,000 to about 1:150,000; optionally from about 1:60,000 to about 1:100,000. According to one embodiment, the weight ratio of MAPD to propane in the olefin stream ranges from about 1:100 to about 1:10,000; typically from about 1:1,000 to about 1:5,000; and optionally from about 1:2,000 to about 1:4,000.

Accordingly, methane, and compounds with a boiling point lower than methane are removed, from the olefin stream before the two-step fractionation. In another embodiment, the two-step fractionation process is downstream from a $C_2$ splitter. Consequently, ethylene and compounds with a boiling point lower than ethylene are removed from the olefin stream before the two-step fractionation. In still another embodiment, the two-step fractionation process is downstream from a deethanizer. Consequently, ethane and compounds with a boiling point lower than ethane are removed from the olefin stream before the two-step fractionation. In another embodiment, the two-step fractionation process of the present invention is downstream from a fractionation tower. Pentane and compounds with a boiling point that is higher than pentene are removed from the olefin stream before the two-step fractionation. Optionally, the two step fractionation process is downstream from a debutanizer. Butane and compounds with a boiling point that his higher than butane are removed from the olefin stream before the two-step fractionation.

The olefin stream is provided along line 30 to the first fractionation tower 32. The first fractionation tower separates a first overhead stream from a first bottoms stream. The first overhead stream of one embodiment comprises propylene. Optionally, the first overhead stream comprises methane, ethylene, and ethane. Other byproducts that are optionally present in the first overhead stream include hydrogen, acetylene dimethyl ether, and carbon monoxide. According to one embodiment, the first overhead stream contains about 30 wt. % or more, preferably about 40 wt. % or more, more preferably about 50 wt. % or more propylene based upon the total weight of the first overhead stream. According to an embodiment, the first overhead stream further comprises from about 0.01 wt. % to about 5 wt. %, typically from about 0.1 wt. % to about 2 wt. %, optionally from about 0.5 wt. % to about 1 wt. % propane based upon the total weight of the first overhead stream. According to another embodiment, the first overhead stream further comprises from about 5 ppbw to about 1000 ppbw, typically from about 20 ppbw to about 800 ppbw, optionally from about 40 ppbw to about 200 ppbw dimethyl ether based upon the total weight of the first olefin stream. In yet another embodiment, the first overhead stream comprises about 1.4 ppm vol or less, preferably about 0.1 ppm vol or less MAPD based upon the total volume of the first overhead stream.

The first overhead stream is conveyed along line 34, optionally, to an additional propylene product recovery step 50. The propylene product recovery step recovers a propylene product stream from other components that are optionally present in the first overhead stream.

If there is methane or compounds with a boiling point higher than methane, the first overhead stream is optionally passed through a demethanizer to separate methane, and other compounds that have a boiling point that is lower than methane, from the propylene in the first overhead stream to form a propylene product stream.

If there is ethylene or compounds with a boiling point higher than ethylene, the first overhead stream is optionally passed through a $C_2$ splitter to separate ethylene, and other compounds that have a boiling point that is lower than ethylene, from the propylene in the first overhead stream. If there is ethane or compounds with a boiling point higher than ethane, the first overhead stream is optionally passed through a deethanizer to separate ethane, and other compounds that have a boiling point that is lower than ethane, from the propylene in the first overhead stream.

Optionally, one or more of these steps are performed to isolate an ethylene product stream from methane, and/or ethane. Thereafter, the propylene and ethylene if any are used in any one of the many applications for propylene and ethylene, if any as represented by box 54.

The first bottoms stream of one embodiment comprises propane, MAPD and $C_4$ olefins. Optionally, the first bottoms stream comprises butane and/or $C_5+$ hydrocarbons. The first bottoms stream is directed along line 36 to a second fractionation tower 38. The second fractionation tower 38 fractionates the first bottoms stream into a second overhead stream and a second bottoms stream. The second overhead stream comprises propane and MAPD in one embodiment. According to one embodiment, the second overhead stream contains about 30 wt. % or less, preferably contains about 20 wt. % or less, more preferably contains about 5 wt. % or less butylene. The second overhead stream of one embodiment further comprises from about 1 wt. % to about 20 wt. %, typically from about 2 wt. % to about 15 wt. %, more typically from about 4 wt. % to about 10 wt. % propane based upon the total weight of the second overhead stream. In yet another embodiment, the second overhead stream further comprises from about 10 wt. % to about 90 wt. %, preferably from about 20 wt. % to about 60 wt. %, more preferably from about 30 wt. % to about 50 wt. % dimethyl ether based upon the total weight of the second overhead stream. In still another embodiment, the second overhead stream comprises about 1 ppmw or more, preferably from about 10 ppmw to about 100 ppmw, more preferably from about 1 ppmw to about 3000 ppmw MAPD based upon the weight of the MAPD in the olefin stream.

The second bottoms stream comprises $C_4$ olefins and optionally comprises butane and $C_5+$ hydrocarbons. According to one embodiment, the second bottoms stream contains about 10 wt. % or more, preferably about 30 wt. % or more, about 50 wt. % or more butylene based upon the total weight of the second bottoms stream. According to another embodiment, the second bottoms stream comprises about 100 ppmw or less, typically from about 10 ppmw to about 70 ppmw, more typically from about 30 ppmw to about 50 ppmw propane based upon the total weight of the second bottoms stream. According to one embodiment, the second bottoms stream further comprises from about 5 ppmw to about 5000 ppmw dimethyl ether, typically from about 50 ppmw to about 3000 ppmw, more typically from about 100 ppmw to about 1000 ppmw dimethyl ether based upon the total weight of the second bottoms stream.

According to another embodiment, the second bottoms stream comprises about 200 ppmw or less, more preferably about 50 ppmw or less, most preferably about 5 ppmw or less MAPD based upon the total weight of the second bottoms stream. The $C_4$ olefins are optionally directed to $C_4$ olefin product recovery step 44. In the $C_4$ olefin product recovery step, $C_4$ olefins are recovered from other components that are optionally present in the $C_4$ olefin stream. Such compounds include butane and $C_5+$ hydrocarbons. $C_5+$ hydrocarbons and butane are further separated by fractionation according to techniques known in the art. Having recovered the $C_4$ olefins, the $C_4$ olefins are then used according to one of the many uses for $C_4$ olefins represented by box 48.

Olefin Product Use

Suitable well-known reaction systems that follow the recovery system primarily take lower value products and convert them to higher value products. For example, the $C_4$ hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel.

Non-limiting examples of reaction systems that take lower value products and convert them to higher value products include U.S. Pat. No. 5,955,640 (converting a four carbon product into butene-1), U.S. Pat. No. 4,774,375 (isobutane and butene-2 alkylated to an alkylate gasoline), U.S. Pat. No. 6,049,017 (dimerization of n-butylene), U.S. Pat. Nos. 4,287, 369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading $C_3$, $C_4$ and $C_5$ Olefinic Streams,* Pet. & Coal, Vol. 37, No. 4 (1995) (dimerizing or oligomerizing propylene, butylene and pentylene), which are all herein fully incorporated by reference.

Other uses for one or more olefin products are disclosed in U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent stream fed to another reactor) PCT WO 01/60770 published Aug. 23, 2001 and U.S. patent application Ser. No. 09/627,634 filed Jul. 28, 2000 (high-pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In another embodiment, olefin(s) produced are directed to, in one embodiment, one or more polymerization processes for producing various polyolefins. (See for example U.S. patent application Ser. No. 09/615,376 filed Jul. 13, 2000 that is herein fully incorporated by reference.)

Polymerization processes include solution, gas phase, slurry phase and a high-pressure process, or a combination thereof. Particularly preferred is a gas phase or a slurry phase polymerization of one or more olefin(s) at least one of which is ethylene or propylene. Polymerization processes include those non-limiting examples described in the following: U.S. Pat. Nos. 4,543,399, 4,588,790, 5,028,670, 5,317,036, 5,352, 749, 5,405,922, 5,436,304, 5,453,471, 5,462,999, 5,616,661, 5,627,242, 5,665,818, 5,677,375, 5,668,228, 5,712,352 and 5,763,543 and EP-A-0 794 200, EP-A-0 802 202, EP-A2-0 891 990 and EP-B-0 634 421 describe gas phase polymerization processes; U.S. Pat. Nos. 3,248,179 and 4,613,484, 6,204,344, 6,239,235 and 6,281,300 describe slurry phase polymerization processes; U.S. Pat. Nos. 4,271,060, 5,001, 205, 5,236,998 and 5,589,555 describe solution phase polymerization processes; and U.S. Pat. Nos. 3,917,577, 4,175, 169, 4,935,397, and 6,127,497 describe high-pressure polymerization processes; all of which are herein fully incorporated by reference.

These polymerization processes utilize a polymerization catalyst that optionally includes any one or a combination of the molecular sieve catalysts discussed above. However, the preferred polymerization catalysts are those Ziegler-Natta, Phillips-type, metallocene, metallocene-type and advanced polymerization catalysts, and mixtures thereof. Non-limiting examples of polymerization catalysts are described in U.S. Pat. Nos. 3,258,455, 3,305,538, 3,364,190, 3,645,992, 4,076,698, 4,115,639, 4,077,904 4,482,687, 4,564,605, 4,659,685, 4,721,763, 4,879,359, 4,960,741, 4,302,565, 4,302,566, 4,302,565, 4,302,566, 4,124,532, 4,302,565, 5,763,723, 4,871,705, 5,120,867, 5,324,800, 5,347,025, 5,384,299, 5,391,790, 5,408,017, 5,491,207, 5,455,366, 5,534,473, 5,539,124, 5,554,775, 5,621,126, 5,684,098, 5,693,730, 5,698,634, 5,710,297, 5,714,427, 5,728,641, 5,728,839, 5,753,577, 5,767,209, 5,770,753 and 5,770,664, 5,527,752, 5,747,406, 5,851,945 and 5,852,146, all of which are herein fully incorporated by reference.

In preferred embodiment, the present invention comprises a polymerizing process of one or more olefin(s) in the presence of a polymerization catalyst system in a polymerization reactor to produce one or more polymer products, wherein the one or more olefin(s) having been made by converting an alcohol, particularly methanol, using a zeolite or zeolite-type molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kPag) to greater than about 1000 psig (3448 kPag), preferably in the range of from about 200 psig (1379 kPag) to about 500 psig (3448 kPag), and more preferably in the range of from about 250 psig (1724 kPag) to about 350 psig (2414 kPag). Typical conditions of polymerization temperature vary from about 0° C. to about 500° C., preferably from about 30° C. to about 350° C., more preferably in the range of from about 60° C. to 250° C., and most preferably in the range of from about 70° C. to about 150° C. In the preferred polymerization process the amount of polymer being produced per hour is greater than 25,000 lbs/hr (11,300 Kg/hr), preferably greater than 35,000 lbs/hr (15,900 Kg/hr), more preferably greater than 50,000 lbs/hr (22,700 Kg/hr) and most preferably greater than 75,000 lbs/hr (29,000 Kg/hr).

The polymers produced by the polymerization processes described above include linear low density polyethylene, elastomers, plastomers, high density polyethylene, low density polyethylene, polypropylene and polypropylene copolymers. The propylene-based polymers produced by the polymerization processes include atactic polypropylene, isotactic polypropylene, syndiotactic polypropylene, and propylene random, block or impact copolymers.

Typical ethylene based polymers have a density in the range of from 0.86 g/cc to 0.97 g/cc, a weight average molecular weight to number average molecular weight ($M_w/M_n$) of greater than 1.5 to about 10 as measured by gel permeation chromatography, a melt index ($I_2$) as measured by ASTM-D-1238-E in the range from 0.01 dg/min to 1000 dg/min, a melt index ratio ($I_{21}/I_2$) (I21 is measured by ASTM-D-1238-F) of from 10 to less than 25, alternatively a $I_{21}/I_2$ of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multilayered constructions in the form of bottles, vessels, large hollow articles, rigid food containers and toys, etc.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

Integrated Process with Up-Front Two Step Distillation

According to another embodiment, there is an integrated process for producing olefins from an oxygenate feed stream. This embodiment is illustrated with reference to FIG. 3. During an oxygenate-to-olefin reaction stage 110, an oxygenate feed stream is converted to a reactor effluent stream that comprises olefins. The reactor effluent stream undergoes reactor effluent quenching stage 112. The reactor effluent quenching stage 112 is described above and produces a quenched effluent stream or a quenched olefin stream that is saturated with water. The quenched olefin stream is optionally compressed in one or more compression stages. According to one embodiment, the quenched olefin stream comprises about 1 wt. % or less, typically from about 500 ppmw to about 0.1 ppmw, optionally from about 5 ppmw to about 50 ppmw water based upon the weight of the quenched olefin stream. The quenched olefin stream comprises the other hydrocarbon components of the reactor effluent stream described above. The quenched olefin stream is provided to a first fractionation-tower 113. The first fractionation tower 113 separates a first overhead stream from a first bottoms stream. The first overhead stream is withdrawn along line 120. The first bottoms stream is withdrawn along line 122. The first overhead stream of one embodiment comprises propylene and other components of the quenched olefin stream that has a boiling point higher than propylene, including without limitation methane, ethane, and ethylene. Other byproducts that, optionally, are present in the first overhead stream include hydrogen, acetylene dimethyl ether, and carbon monoxide.

According to one embodiment, the first overhead stream optionally comprises about 5 wt. % or less, preferably about 1 wt. % or less, more preferably about 0.5 wt. % or less, typically from about 5 to about 0.5 wt. % propane based upon the amount of propane in the quenched olefin stream. The first overhead stream optionally comprises about 10 wt. % or less, preferably about 1 wt. % or less, more preferably about 1 ppmw or less, typically from about 0.1 ppmw to about 1 wt. % dimethyl ether based upon the amount of dimethyl ether in the quenched olefin stream. The first overhead stream optionally comprises about 3,000 ppbw or less, preferably about 100 ppbw or less, more preferably about 10 ppbw or less, typically from about 5 ppbw to about 50 ppbw MAPD based upon the amount of MAPD in the quenched olefin stream.

The first overhead stream is conveyed along line 120 to a washing and drying stage 114. The wash and drying stage 114 is performed in accordance with the foregoing description of the washing and drying. Following the washing and drying stage 114, the dried first overhead stream is passed to a $C_2$ and $C_3$ olefin product recovery stage 116. The $C_2$ and $C_3$ olefin product recovery stage 114 is done in accordance with the foregoing description and in accordance with general principles of olefin recovery. Following, olefin recovery, the olefin products are used according to the many product applications and uses for an olefin product stream including, without limitation, those applications and end uses described above.

As noted above, the $C_2$ and $C_3$ olefins are separated in a first overhead stream from MAPD in a first bottoms stream. The first bottoms stream of one embodiment comprises dimethyl ether, propane, MAPD, $C_4$ olefins, butane and $C_5$+ hydrocarbons. Other components of the effluent stream that has a boiling point greater than the boiling point of propylene are optionally found in the first bottoms stream. The first bottoms stream is directed along line 122 to a second fractionation tower 124. The second fractionation tower 124 fractionates the first bottoms stream into a second overhead stream and a second bottoms stream. The second overhead stream comprises propane and MAPD in one embodiment. Typically, the second overhead stream comprises dimethyl ether. The second overhead stream optionally comprises any component of the quenched effluent stream that has a relative volatility lower than butylene and higher than propylene. The second bottoms stream comprises $C_4$ olefins, butane and $C_5$+ hydrocarbons. The second overhead stream optionally comprises any component of the quenched effluent stream that has a relative volatility higher than butylene.

According to another embodiment, the second bottoms stream comprises about 1,000 ppmw or less, preferably about 100 ppmw or less, more preferably about 50 ppmw or less propane based upon the amount of propane in the quenched olefin stream. According to another embodiment, the second bottoms stream comprises about 3,000 ppmw or less, preferably about 1,000 ppmw or less, more preferably about 500 ppmw or less dimethyl ether based upon the amount of dimethyl ether in the quenched olefin stream. According to another embodiment, the second bottoms stream comprises about 100 ppmw or less, preferably about 50 ppmw or less, more preferably about 1 ppmw or less MAPD based upon the amount of MAPD in the quenched olefin stream.

The $C_4$ olefins are optionally directed to a $C_4$ olefin product recovery stage 130. In the $C_4$ olefin product recovery stage, $C_4$ olefins are recovered from other components that are optionally present in the second bottoms stream. Such compounds include butane and $C_5$+ hydrocarbons. $C_5$+ hydrocarbons and butane is further separated by fractionation according to techniques that are generally understood in the industry. Having recovered the $C_4$ olefin products, the $C_4$ olefin products pass to a $C_4$ olefin product use stage. In the $C_4$ product use stage 132, $C_4$ olefin products are used in the many applications and end uses for $C_4$ olefin products including without limitation, the uses and applications described above. As described above, the present invention provides a process for removing MAPD from a propylene stream and/or a butylene stream by two step fractionation. The two step fractionation is located in the product recovery section of an oxygenate-to-olefin process according to one embodiment. In another embodiment, it is located in the stage of washing and drying. In either instance, the MAPD is not necessarily hydrogenated. MAPD is therefore recoverable from the process.

The foregoing description of the invention including but not limited to drawing and example are intended to illustrate one or more embodiments of the invention and are non-limiting. While the invention has been illustrated an described herein in terms of the advantages, features, and applications disclosed, it will be apparent to a person of ordinary skill in the art that the invention can be used in other instances. Other modifications and improvements can be made without departing from the scope of the invention.

I claim:

1. A process for producing a stream of propylene and a stream of butylene from an olefin stream, the process comprising the steps of:
    (a) providing a reactor effluent from an oxygenates-to-olefins process as an olefin stream comprising propylene, MAPD, dimethyl ether, and butylene;
    (b) fractionating the olefin stream thereby producing a first overhead stream and a first bottoms stream, such that the first overhead stream comprises propylene, comprises from about 5 ppbw to about 1000 ppbw dimethyl ether based on the weight of the first overhead stream, and is substantially free of MAPD, and such that the first bottoms stream comprises MAPD and butylene, wherein no propane is added to said reactor effluent before this olefin stream is fractionated in this step (b); and
    (c) fractionating the first bottoms stream thereby producing a second overhead stream and a second bottoms stream, such that the second overhead stream comprises MAPD and such that the second bottoms stream comprises about 10 wt. % or more butylene, wherein the second bottoms stream is substantially free of MAPD.

2. The process of claim 1, wherein the first overhead stream contains about 30 wt. % or more propylene based upon the weight of the first overhead stream.

3. The process of claim 1, wherein the first overhead stream contains about 40 wt. % or more propylene based upon the weight of the first overhead stream.

4. The process of claim 1, wherein the first overhead stream further comprises from about 0.01 wt. % to about 5 wt. % propane based upon the weight of the first overhead stream.

5. The process of claim 1, wherein the first overhead stream further comprises from about 0.1 wt. % to about 2 wt. % propane based upon the weight of the first overhead stream.

6. The process of claim 1, wherein the first overhead stream further comprises from about 20 ppbw to about 800 ppbw dimethyl ether based upon the weight of the first overhead stream.

7. The process of claim 1, wherein the first overhead stream further comprises about 1.4 ppm vol or less MAPD based upon the volume of the first overhead stream.

8. The process of claim 1, wherein the second bottoms stream contains about 30 wt. % or more butylene based upon the weight of the second bottoms stream.

9. The process of claim 1, wherein the second bottoms stream contains about 50 wt. % or more butylene based upon the weight of the second bottoms stream.

10. The process of claim 1, wherein the second bottoms stream further comprises from about 0.1 ppmw to about 100 ppmw propane based upon the weight of the second bottoms stream.

11. The process of claim 1, wherein the second bottoms stream further comprises from about 10 ppmw to about 70 ppmw propane based upon the weight of the second bottoms stream.

12. The process of claim 1, wherein the second bottoms stream further comprises from about 5 ppmw to about 5000 ppmw dimethyl ether based upon the weight of the second bottoms stream.

13. The process of claim 1, wherein the second bottoms stream further comprises from about 50 ppmw to about 3000 ppmw dimethyl ether based upon the weight of the second bottoms stream.

14. The process of claim 1, wherein the second bottoms stream comprises about 200 ppmw or less MAPD based upon the weight of the second bottoms stream.

15. The process of claim 1, wherein the second bottoms stream comprises about 50 ppmw or less MAPD based upon the weight of the second bottoms stream.

16. The process of claim 1, wherein the second overhead stream contains about 30 wt. % or less butylene based upon the weight of the second overhead stream.

17. The process of claim 1, wherein the second overhead stream contains about 20 wt. % or less butylene based upon the weight of the second overhead stream.

18. The process of claim 1, wherein the second overhead stream further comprises from about 1 ppmw to about 20 wt. % propane based upon the weight of the second overhead stream.

19. The process of claim 1, wherein the second overhead stream further comprises from about 2 wt. % to about 15 wt. % propane based upon the weight of the second overhead stream.

20. The process of claim 1, wherein the second overhead stream further comprises from about 10 wt. % to about 90 wt. % dimethyl ether based upon the weight of the second overhead stream.

21. The process of claim 1, wherein the second overhead stream further comprises from about 20 wt. % to about 60 wt. % dimethyl ether based upon the weight of the second overhead stream.

22. The process of claim 1, wherein the second overhead stream comprises about 1 ppmw or more MAPD based upon the weight of MAPD in the olefin stream.

23. The process of claim 1, wherein the second overhead stream comprises from about 10 ppmw to about 1,000 ppmw MAPD based upon the weight MAPD in the olefin stream.

24. The process of claim 1, wherein the olefin stream comprises about 1 wt. % or less water based upon the weight of the olefin stream.

25. The process of claim 1, wherein the olefin stream comprises from about 0.1 ppmw to about 500 ppmw water based upon the weight of the olefin stream.

26. A process for separating MAPD from a propylene stream,
(a) providing a first stream derived from a reactor effluent from an oxygenates-to-olefins process, said first stream comprising propylene, MAPD, and dimethyl ether and wherein no propane is added to said reactor effluent before said first stream derived from said effluent is separated in step (b); and
(b) separating said first stream into a second stream and a third stream, such that the second stream contains propylene and such that the third stream contains MAPD and dimethyl ether, wherein the concentration of MAPD in the second stream is less than 10 ppmw based upon the weight of the second stream, the second stream further comprises from about 5 ppbw to about 1000 ppbw dimethyl ether based upon the weight of the second stream, and the concentration of propylene in the third stream is less than 1 ppmw based upon the weight of the third stream.

27. The process of claim 26, wherein the second stream contains about 30 wt. % or more propylene based upon the weight of the second stream.

28. The process of claim 26, wherein the second stream further comprises from about 0.01 wt. % to about 5 wt. % propane based upon the weight of the second stream.

29. The process of claim 26, wherein the second stream further comprises about 1.4 ppm vol or less MAPD based upon the volume of the second stream.

30. The process of claim 26, wherein the first stream further comprises propane, butylene and higher boiling point compounds, the process further comprising the step of separating the third stream into a fourth stream and a fifth stream, the fourth stream comprising propane, dimethyl ether and MAPD, the fifth stream comprising butylene.

31. The process of claim 30, wherein the fifth stream contains about 10 wt. % or more butylene based upon the weight of the fifth stream.

32. The process of claim 30, wherein the fifth stream further comprises from about 0.1 ppmw to about 100 ppmw propane based upon the weight of the fifth stream.

33. The process of claim 30, wherein the fifth stream further comprises from about 5 ppmw to about 5000 ppmw dimethyl ether based upon the weight of the fifth stream.

34. The process of claim 30, wherein the fifth stream comprises about 200 ppmw or less MAPD based upon the weight of the fifth stream.

35. The process of claim 30, wherein the fourth stream contains about 30 wt. % or less butylene based upon the weight of the fourth stream.

36. The process of claim 30, wherein the fourth stream further comprises from about 1 wt. % to about 20 wt. % propane based upon the weight of the fourth stream.

37. The process of claim 30, wherein the fourth stream further comprises from about 10 wt. % to about 90 wt. % dimethyl ether based upon the weight of the fourth stream.

38. The process of claim 30, wherein the fourth stream comprises less than about 1 ppmw MAPD based upon the weight of the MAPD in the first stream.

39. The process of claim 30, wherein the first stream comprises about 1 wt. % or less water based upon the weight of the first stream.

40. The process of claim 1, wherein the first overhead stream comprises about 1 wt. % or less propane.

* * * * *